US008115501B2

(12) United States Patent
Albertson et al.

(10) Patent No.: US 8,115,501 B2
(45) Date of Patent: Feb. 14, 2012

(54) ELECTRO-MECHANICAL FLUID SENSOR (75) Inventors: William C. Albertson, Clinton Township, MI (US); Joseph J. Moon, Clawson, MI (US)

(73) Assignee: GM Global Technology Operations LLC

( * ) Notice: Subject to any disclaimer, the term of this patent is extended or adjusted under 35 U.S.C. 154(b) by 428 days.

(21) Appl. No.: 12/392,553

(22) Filed: Feb. 25, 2009

(65) Prior Publication Data

US 2010/0127718 A1 May 27, 2010

Related U.S. Application Data (63) Continuation-in-part of application No. 12/276,876, filed on Nov. 24, 2008.

(51) Int. Cl.
*G01R 27/22* (2006.01)

(52) U.S. Cl. .......................... 324/694; 210/243
(58) Field of Classification Search .................. 324/415, 324/694; 123/25 J; 210/243
See application file for complete search history.

(56) References Cited

U.S. PATENT DOCUMENTS

| | | | |
|---|---|---|---|
| 3,656,140 A | 4/1972 | Gruber et al. | |
| 4,168,693 A | 9/1979 | Harrison | |
| 4,627,272 A | 12/1986 | Wright | |
| 4,637,351 A * | 1/1987 | Pakula | 123/25 J |
| 5,381,874 A | 1/1995 | Hadank et al. | |
| 5,442,671 A | 8/1995 | Wollschlager et al. | |
| 5,808,471 A | 9/1998 | Rooke et al. | |
| 5,823,295 A | 10/1998 | Griffith et al. | |
| 5,853,068 A | 12/1998 | Dixon et al. | |
| 6,207,045 B1 | 3/2001 | Jiang | |
| 6,591,798 B2 | 7/2003 | Hendriksma et al. | |
| 7,030,580 B2 | 4/2006 | Hoff | |
| 7,178,499 B2 | 2/2007 | Wolf et al. | |
| 7,677,086 B2 | 3/2010 | Albertson et al. | |
| 2005/0022784 A1 | 2/2005 | Wolf et al. | |
| 2006/0169229 A1 * | 8/2006 | Ervin et al. | 123/90.11 |
| 2008/0093172 A1 | 4/2008 | Albertson et al. | |
| 2008/0223114 A1 | 9/2008 | Albertson et al. | |
| 2008/0250851 A1 | 10/2008 | Keller et al. | |
| 2008/0282786 A1 | 11/2008 | Van Weelden et al. | |
| 2009/0188755 A1 | 7/2009 | Staley et al. | |

OTHER PUBLICATIONS

U.S. Appl. No. 12/276,876, filed Nov. 24, 2008, David R. Staley, et al.
Han, T. et al., "Engine Oil Viscometer Based on Oil Pressure Sensor," SAE Technical Paper Series, Jan. 2006-701, 2006 World Congress, Apr. 3-6, 2006, 9 pages.

* cited by examiner

*Primary Examiner* — Vincent Q Nguyen (57) ABSTRACT

A sensor system includes a sensor and a control module. The sensor includes an electrically actuated moving member. The sensor is in fluid communication with a reservoir of a separator that separates a first fluid from a fuel. The control module selectively causes current to be supplied to the sensor to actuate the member. The control module measures the current and determines a parameter of the current. The control module identifies one of presence and absence of the first fluid in the reservoir based on the parameter.

20 Claims, 7 Drawing Sheets

ELECTRO-MECHANICAL FLUID SENSOR

CROSS-REFERENCE TO RELATED APPLICATIONS

This application is a continuation-in-part of U.S. patent application Ser. No. 12/276,876, filed on Nov. 24, 2008, and entitled "Oil Condition Sensing Methods and Systems." The disclosure of the above application is incorporated herein by reference in its entirety.

FIELD

The present disclosure relates to fluid sensors and more particularly to electro-mechanical fluid sensor systems and methods for controlling electro-mechanical fluid sensor systems.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Diesel motors combust diesel fuel in combustion chambers to generate torque that can be used to propel a vehicle. If water infiltrates the diesel fuel, the lubricity of the diesel fuel may be reduced, leading to increased wear for components of the engine. For example, a fuel delivery system, which delivers the diesel fuel to the combustion chambers, may include tightly fitting components that rely on the lubricating properties of the diesel fuel. For example only, water intermixed with fuel flowing at high velocity may abrade highly polished valve seats and fine nozzle orifices.

Further, water may contain biological and chemical impurities, which may cause corrosion of engine components. Water infiltration may also have negative effects in engines using other types of fuel, such as gasoline. Various engines may therefore include a water separator that attempts to remove water from the fuel supply.

Figure 1:
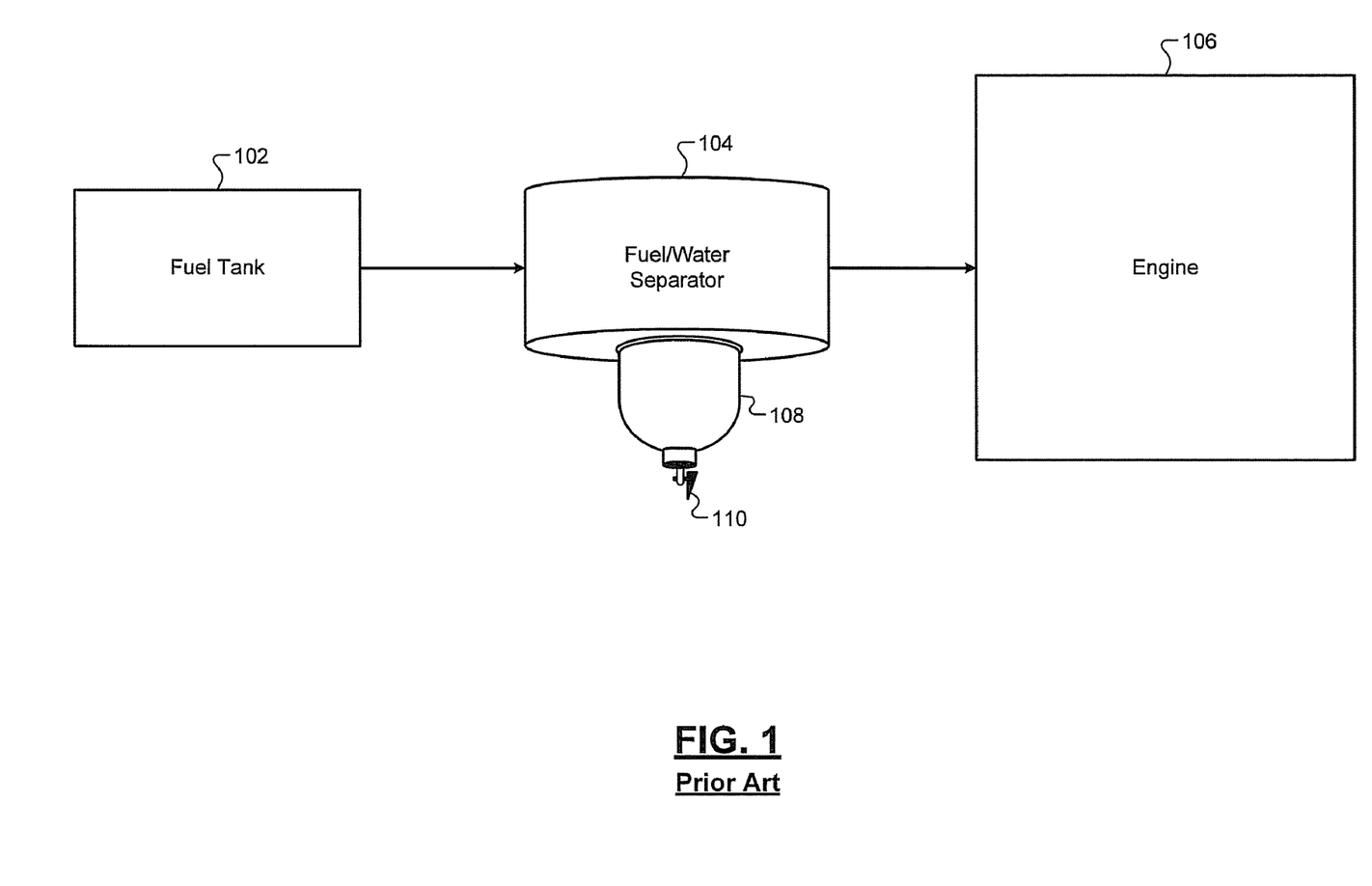
FIG. 1 is a functional block diagram of an exemplary engine system including a water separator according to the prior art.

Referring now to FIG. 1, an exemplary engine system including a water separator is shown. A fuel tank 102 provides fuel to a fuel/water separator 104. The fuel/water separator 104 separates water from the fuel and directs the fuel to an engine 106. The fuel/water separator 104 includes a bowl 108 in which the separated water collects.

The bowl 108 may include a valve 110 that can be opened to drain water from the bowl 108. The bowl 108 may be clear to allow visual inspection of the water level in the bowl 108. Traditionally, periodic inspection of the bowl 108 is required to ensure a low water level in the bowl 108. Once the bowl 108 fills with water, operation of the fuel/water separator 104 may be impaired.

Some systems may include electrodes in the bowl 108. A voltage potential is applied to the electrodes, and, because water is more conductive than fuel, the presence of water is indicated by a higher current flow between the electrodes. However, over time, electrodes may corrode in the presence of water and other impurities, which adversely affects their electrical conductivity.

SUMMARY

A sensor system includes a sensor and a control module. The sensor includes an electrically actuated moving member. The sensor is in fluid communication with a reservoir of a separator that separates a first fluid from a fuel. The control module selectively causes current to be supplied to the sensor to actuate the member. The control module measures the current and determines a parameter of the current. The control module identifies one of presence and absence of the first fluid in the reservoir based on the parameter.

A method includes selectively causing current to be supplied to a sensor to actuate a movable member of the sensor. The sensor is in fluid communication with a reservoir of a separator that separates a first fluid from a fuel. The method also includes measuring the current supplied to the sensor, determining a parameter of the current, and identifying one of presence and absence of the first fluid in the reservoir based on the parameter.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

Figure 2:
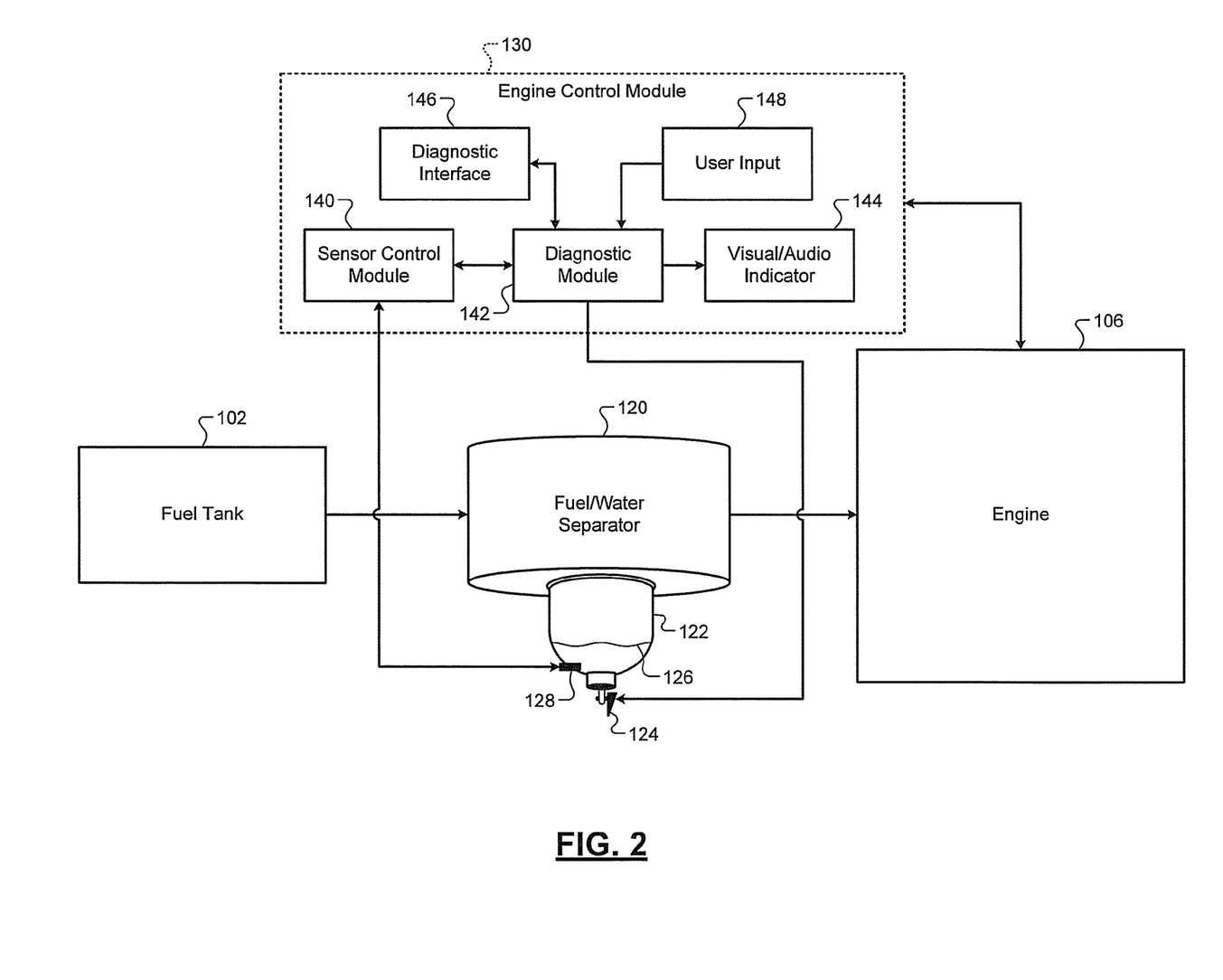
FIG. 2 is a functional block diagram of an exemplary engine system including a water separator according to the principles of the present disclosure.

Referring now to FIG. 2, a functional block diagram of an exemplary engine system is presented. The fuel tank 102 provides fuel, such as gasoline or diesel fuel, to a fuel/water separator 120. The fuel/water separator 120 separates fuel from water, provides fuel to the engine 106, and directs water into a bowl 122. The bowl 122 may include a valve 124, which allows water to be emptied from the bowl 122.

For example only, a water line 126 is shown, indicating that water is present below the water line 126 while fuel is present above the water line 126 (assuming that water is denser than the fuel). A sensor 128 may be installed in the bowl 122 to detect the presence of water. An engine control module 130 controls operation of the engine 106. For example, the engine control module 130 may control actuators (not shown) within the engine 106 to produce a torque as requested by a driver.

The engine control module 130 may include a sensor control module 140 that controls and receives signals from the sensor 128. At various times, a diagnostic module 142 commands the sensor control module 140 to take a reading from the sensor 128. For example only, the diagnostic module 142 may issue this command on a periodic schedule. For example only, the schedule may be altered based on sensed driving habits, such as average engine run time.

The sensor control module 140 may interpret readings from the sensor 128 to determine whether water is present in the bowl 122. The level of water that the sensor 128 detects is determined by where in the bowl 122 the sensor 128 is placed. The diagnostic module 142 may generate a visual/audio indicator 144 when water is detected. For example only, the visual/audio indicator 144 may include a check engine light or a digital instrument panel display.

The diagnostic module 142 may also set a diagnostic trouble code, which may be stored in a diagnostic interface 146. The diagnostic interface 146 may be queried by diagnostic tools, such as at a dealership or repair facility. The diagnostic interface 146 may record the times during which water is detected, and provide these to the diagnostic tools.

User input 148 may instruct the diagnostic module 142 to command a new reading from the sensor 128. The user input 148, for example only, may include a button. A user may actuate the user input 148 after water has been drained from the bowl 122. In various implementations, the valve 124 may be controlled by the diagnostic module 142, such as with electrical or vacuum signals. Control of the valve 124 may also be performed via the diagnostic interface 146.

Figure 3:
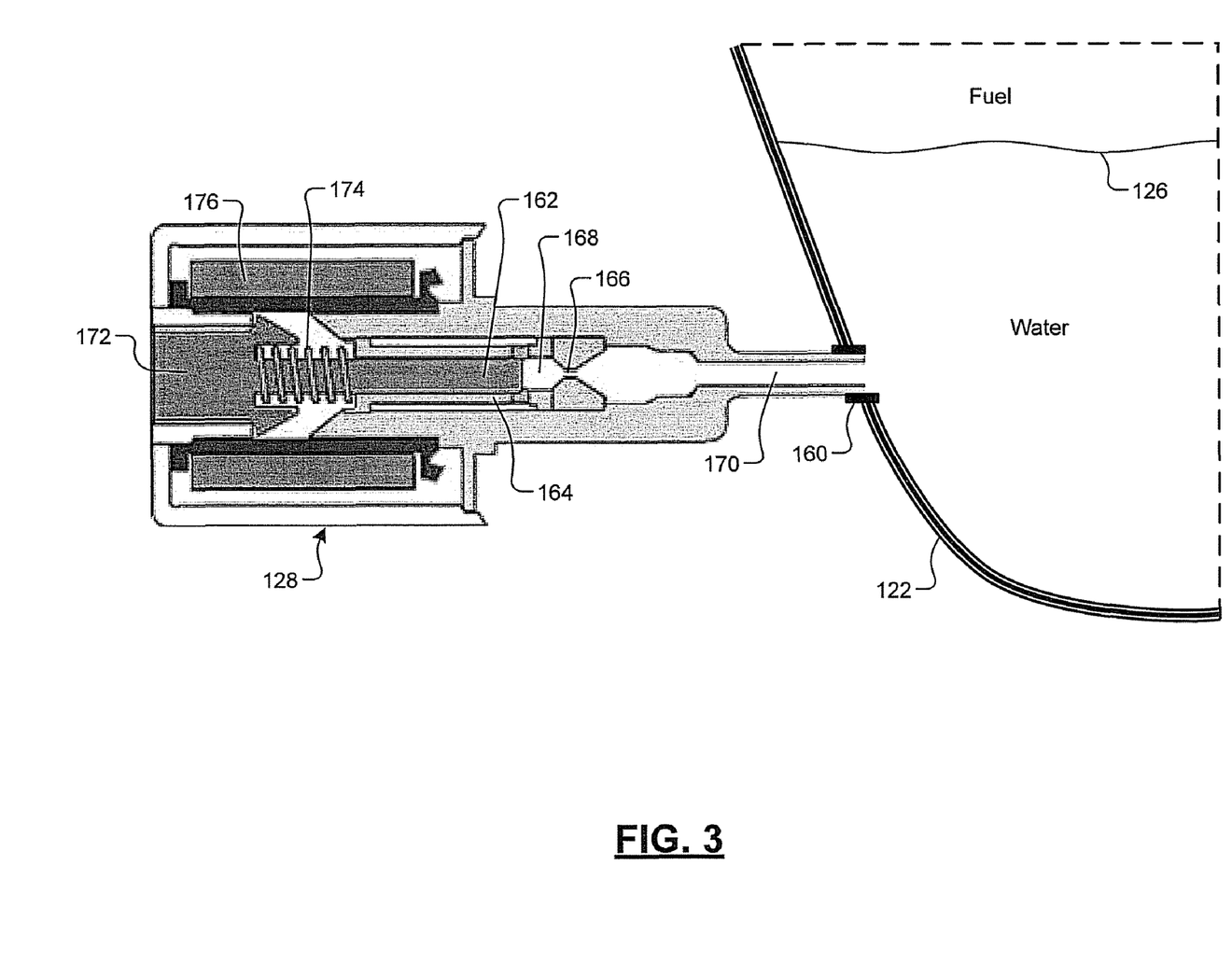
FIG. 3 is a partial cross sectional view of a bowl and an exemplary implementation of a sensor according to the principles of the present disclosure.

Referring now to FIG. 3, a partial cross sectional view is presented of the bowl 122 and an exemplary implementation of the sensor 128. The sensor 128 may be coupled to the bowl 122 via a gasket 160. A piston 162 rides within a sleeve 164 to pull liquid through an orifice 166 into a chamber 168. The liquid may be pulled into the chamber 168 through a channel 170 from the bowl 122.

In various implementations, the length of the channel 170 may be reduced, and/or the channel 170 may be removed entirely. For example only, the orifice 166 may be defined at the wall of the bowl 122. The piston 162 is connected to an armature 172. The armature 172 is biased to a first position by a coil return spring 174. When a current is applied to windings 176, the resulting electromagnetic field actuates the armature 172 to a second position in opposition to the return spring 174.

As the armature 172 moves from the first position to the second position, the piston 162 presses the fluid from the chamber 168 through the orifice 166. For fluids with higher viscosities, the fluid is more difficult to push from the chamber 168 through the orifice 166. This change in viscosity may be evidenced by a change in the electrical characteristics of the sensor 128, as described in more detail with respect to FIG. 4.

Figure 4:
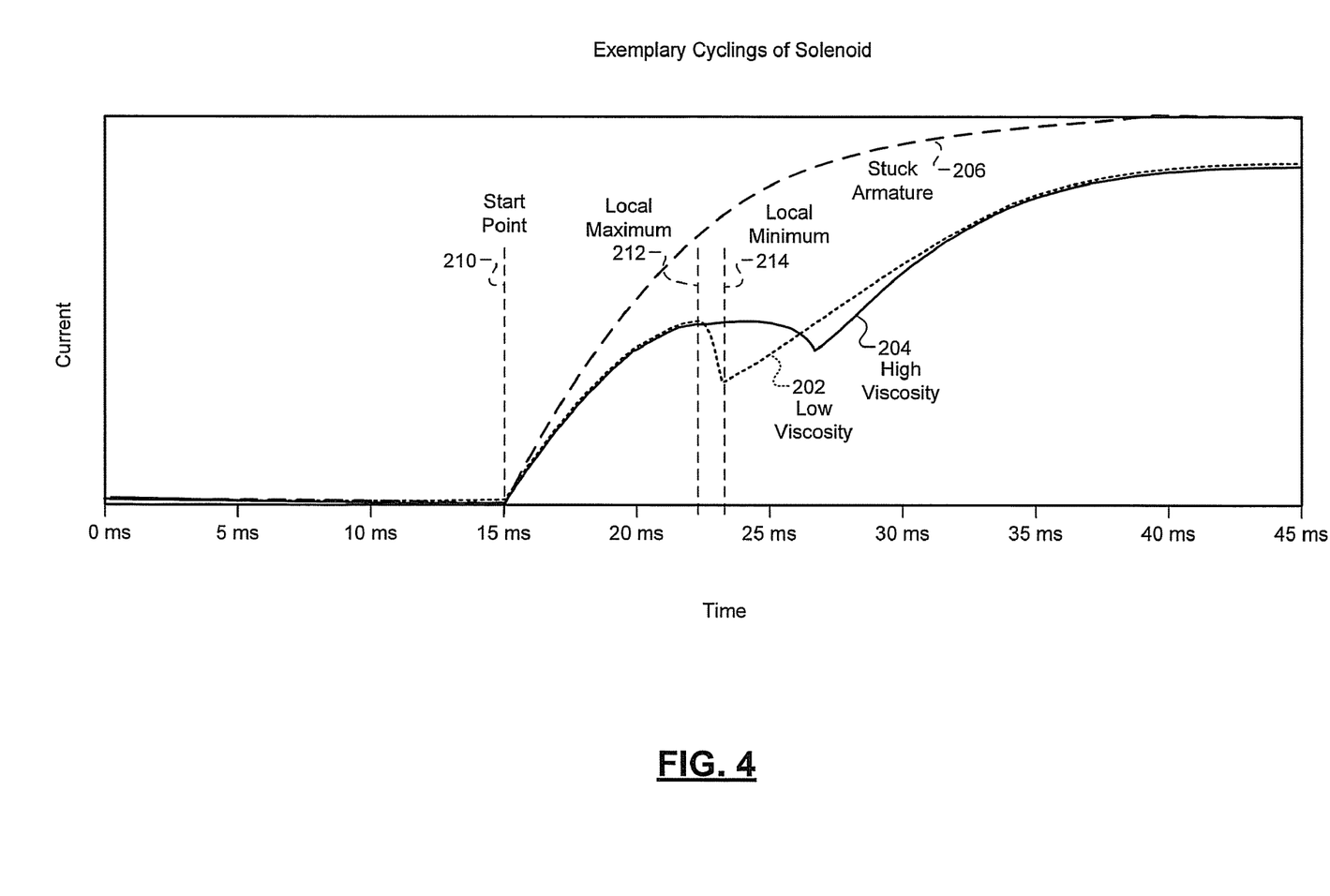
FIG. 4 is a graphical depiction of three exemplary traces of current of a solenoid according to the principles of the present disclosure.

Referring now to FIG. 4, three exemplary traces 202, 204, and 206 of the current of a solenoid are shown. Trace 202 corresponds to a low viscosity, trace 204 corresponds to a higher viscosity, and trace 206 corresponds to an infinite viscosity. An infinite, or extremely high, viscosity has the same effect as if the armature of the solenoid were mechanically stuck. Traces 202 and 204 each include a notch in the current. By contrast, trace 206 lacks the notch. For traces similar to trace 206, the notch time may be considered to be infinite, or set to a maximum amount of time.

The location of the notch is an indication of the viscosity of the fluid with which the solenoid is interfacing. Because the solenoid piston displaces fluid in front of the piston, hydraulic resistance is caused by the viscous fluid moving through a restrictive flow passage (such as an orifice). This hydraulic resistance exerts a pressure on the face of the piston, which resists armature movement and changes the current response characteristics of the solenoid.

At a start point 210, the solenoid is instructed to actuate. This may be initiated by a trigger signal that arrives at the start point 210. For purposes of illustration, trace 202 will be analyzed. After the start point 210, the current of trace 202 begins increasing. At a first point 212, trace 202 transitions from increasing to decreasing. The first point 212 is therefore a local maximum.

Trace 202 then decreases until a second point 214, when trace 202 transitions from decreasing back to increasing. The second point 214 is therefore a local minimum. The armature of the solenoid begins moving at the first point 212 and stops moving at the second point 214. The measured current decreases between the first and second points 212 and 214 because the moving armature creates a back electromotive force (EMF) that opposes the electrical potential.

The amount of time elapsed between the start point 210 and the second point 214 is referred to as the notch time. The notch time of trace 204 is greater than the notch time of trace 202, indicating that the solenoid is interfacing with a higher viscosity fluid in trace 204. The notch time of trace 206 may be reported as a predetermined maximum value. For example, the notch time for trace 206 may be reported as 45 ms.

Figure 5:
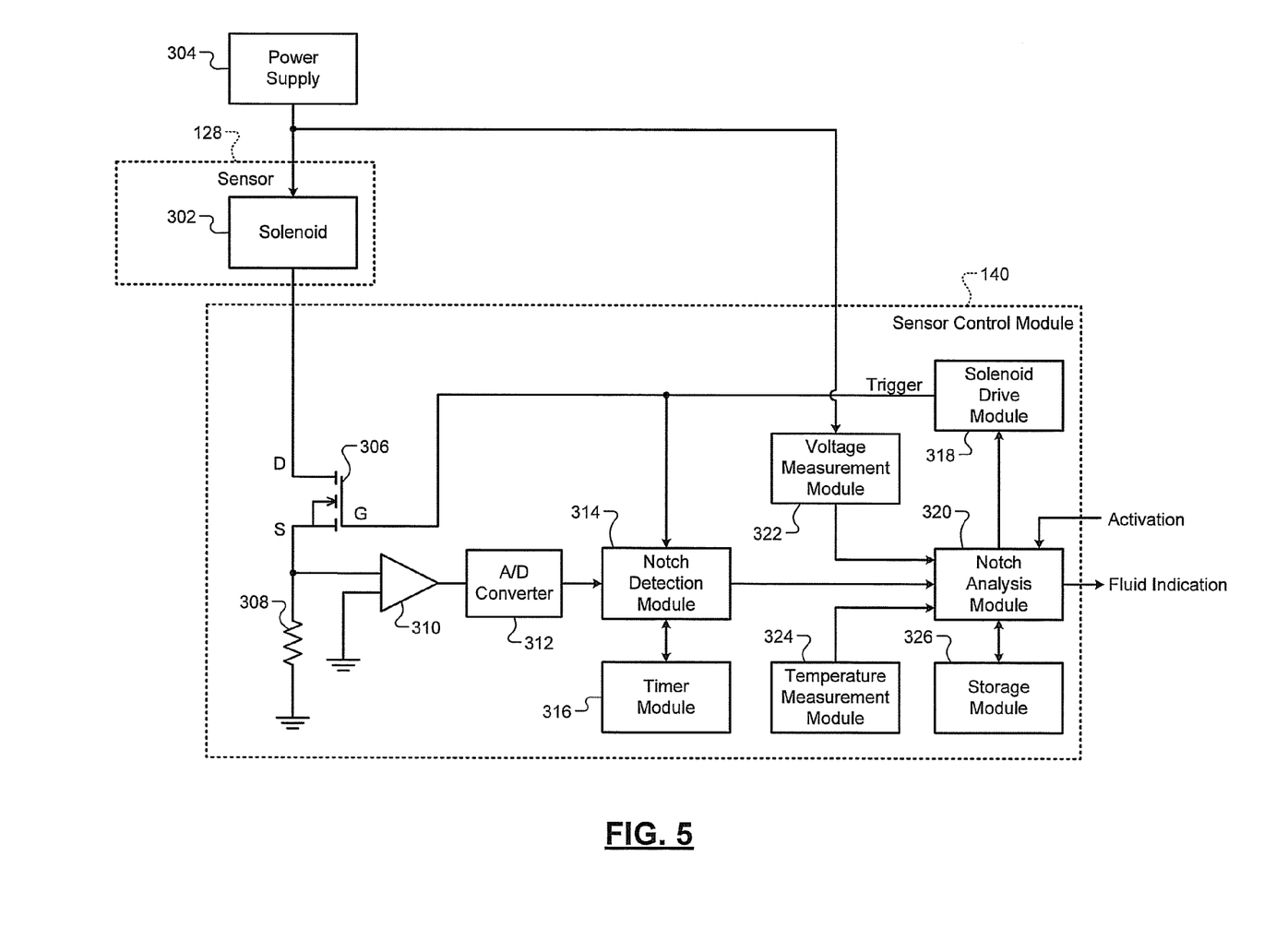
FIG. 5 is a functional block diagram of a sensor system including an exemplary implementation of a sensor control module according to the principles of the present disclosure.

Referring now to FIG. 5, a functional block diagram of a sensor system including an exemplary implementation of the sensor control module 140 is presented. The sensor 128 includes an electrically-operated element that interfaces with fluid. For example only, the sensor 128 may include a solenoid 302 that interfaces with the fluid. Alternatively, the sensor 128 may include a plate that is moved through the fluid by an electric motor. In various implementations, a rotating or translating plate may be less expensive to implement than a solenoid.

The solenoid 302 may be connected to a power supply 304. In various implementations, the power supply 304 may be a vehicle battery, which may also provide power to the sensor control module 140. Current flow from the power supply 304 through the solenoid 302 is regulated by a switch 306, such as a transistor. In various implementations, the transistor may include an n-channel metal-oxide semiconductor field-effect transistor (MOSFET) having a source (S) terminal, a drain (D) terminal, and a gate (G) terminal.

The current flowing through the switch 306 may be routed through a shunt resistor 308 before reaching a reference potential, such as ground. The shunt resistor 308 develops a voltage potential proportional to current flow. An amplifier 310 amplifies the voltage potential across the shunt resistor

308. Alternatively, other current sensing devices, such as a Hall effect sensor, may be used to determine the current flowing through the solenoid 302. An output of the amplifier 310 may be converted to a digital value by an analog-to-digital (A/D) converter 312. The digital value is a representation of the current flowing through the solenoid 302.

A notch detection module 314 may evaluate the digital signal from the A/D converter 312 to determine the time at which the notch of the solenoid current occurs with respect to a trigger signal. The trigger signal may be generated when the solenoid is instructed to actuate. The trigger signal may be generated by a solenoid drive module 318. For example only, the notch detection module 314 may initialize a timer in a timer module 316 when the trigger signal is received. The time elapsed in the timer module 316 between the trigger signal arriving and the current notch being detected is the notch time.

The solenoid drive module 318 may provide the trigger signal to the gate of the switch 306, thereby allowing current to flow through the solenoid 302. A notch analysis module 320 may receive an activation signal, such as from the diagnostic module 142 of FIG. 2. Based on this activation signal, the notch analysis module 320 may instruct the solenoid drive module 318 to produce the trigger signal. The notch analysis module 320 may instruct the solenoid drive module 318 to actuate the solenoid 302 multiple times to circulate fluid and ensure a representative sample is analyzed. In various implementations, the final notch time may be selected, or an average of selected ones of the notch times may be used.

A voltage measurement module 322 may measure a voltage of the power supply 304. The notch analysis module 320 may adjust the notch time based on the measured voltage. For example only, a higher voltage from the power supply 304 may be expected to decrease the notch time. The notch analysis module 320 may therefore increase the indicated notch time when the measured voltage is higher.

Further, viscosity may vary with temperature. Therefore, a temperature measurement module 324 may be implemented. For example only, fluid temperature may be modeled, measured directly, and/or inferred from other temperature measurements, such as engine coolant temperature. The temperature measurement module 324 may receive data from a temperature sensor (not shown), such as a thermocouple, associated with the solenoid 302. In various implementations, the temperature sensor may be implemented in the sensor 128.

Alternatively, temperature readings from other systems may be used. For example only, the temperature measurement module 324 may receive a temperature used by a fuel injection system for fuel injection control. In various implementations, temperature may be estimated based on resistance of the windings in the solenoid 302. The notch analysis module 320 may normalize the notch time based on temperature. For example only, if viscosity decreases as temperature increases, the notch analysis module 320 may increase the indicated notch time when the measured temperature is higher.

The notch analysis module 320 may use the normalized notch time to make determinations about the fluid interfacing with the sensor 128. For example only, a predetermined value may be stored in a storage module 326. If the normalized notch time is greater than the predetermined value, indicating that viscosity is relatively high, the notch analysis module 320 may report that fuel, instead of water, is present. Conversely, when the normalized notch time is less than or equal to the predetermined value, the notch analysis module 320 may report that water is present at the sensor 128.

In various implementations, the storage module 326 may store multiple values to differentiate between water, air, and/or multiple types of fuel. For example only, different types of diesel fuel, including biodiesel, may have different characteristic notch times. The notch analysis module 320 may report the type of fuel detected as well as the presence of water. The values in the storage module 326 may be stored in a lookup table. These values may be determined empirically and/or estimated based on sensor characteristics, such as solenoid geometries, orifice size, and fluid properties.

Figure 6:
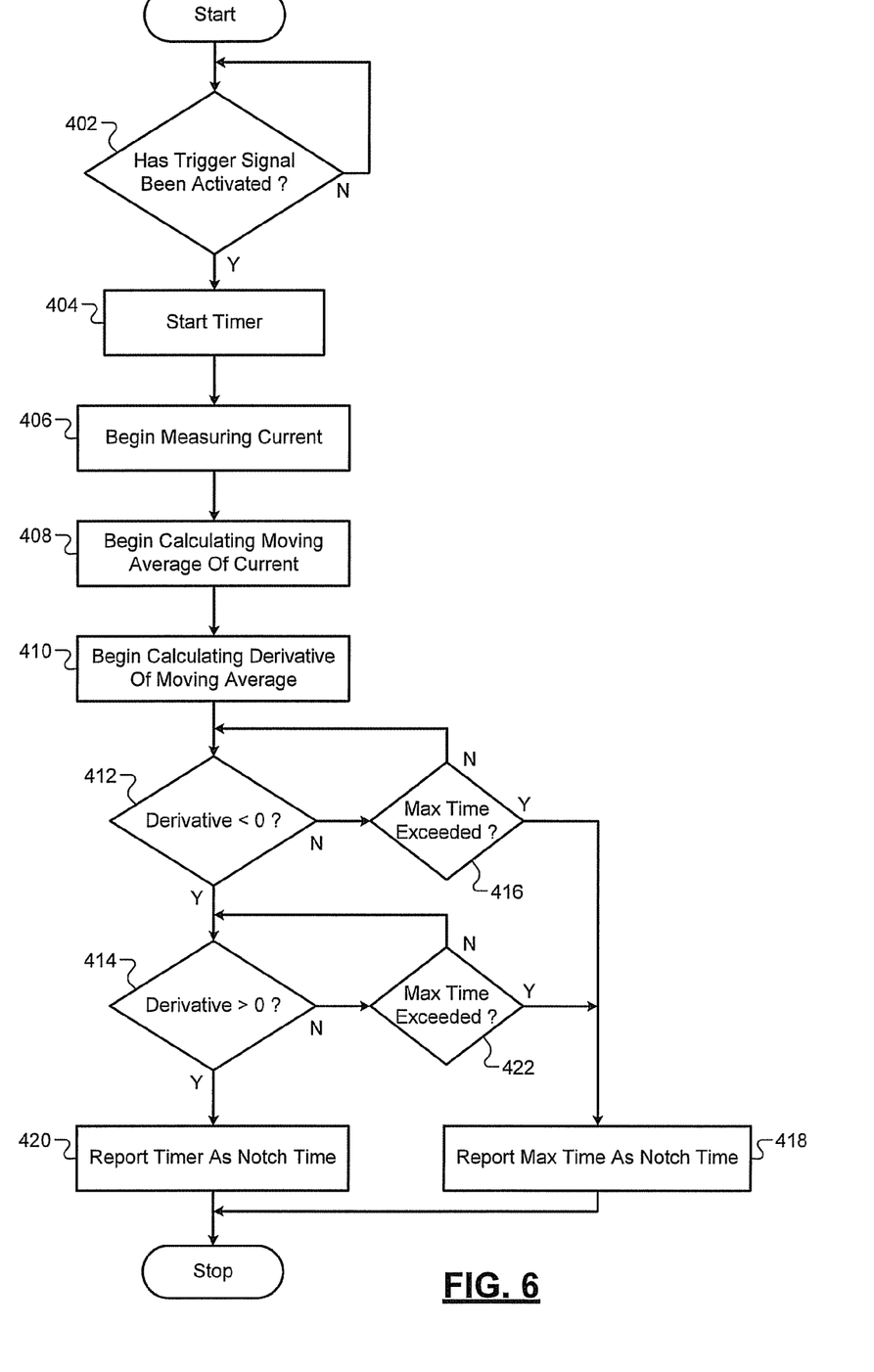
FIG. 6 is a flowchart depicting exemplary steps performed in analyzing a current signal according to the principles of the present disclosure.

Referring now to FIG. 6, a flowchart depicts exemplary steps performed in analyzing the signal from the A/D converter 312 of FIG. 5. Control begins in step 402, where control determines whether the trigger signal has been activated. If so, control continues in step 404; otherwise, control remains in step 402. In step 404, a timer is started and control continues in step 406.

In step 406, control begins measuring current flowing through the solenoid. Control continues in step 408, where control begins calculating a moving average of the current. The moving current average may be calculated in order to decrease the false detection of a local maximum or local minimum. In this way, small disturbances in the current signal, such as those due to noise, will not be incorrectly detected as a change in direction of the current.

For example only, the moving average may be a two-point moving average. The moving average may be calculated as a prior moving average or as a central moving average, which uses data taken after the point being calculated. In addition, the moving average may be a simple moving average or a weighted moving average, and the weighting may be linear or exponential.

Control continues in step 410, where control begins calculating a derivative of the moving average. For example only, control may calculate the derivative as the difference between the current moving average value and the previous moving average value divided by the time between the moving average values. Control continues in step 412, where control determines whether the derivative has decreased below zero. If so, control transfers to step 414; otherwise, control transfers to step 416. For example only, control may transfer to step 414 only when multiple sequential derivatives remain below zero.

In step 416, control determines whether the timer is greater than a predetermined maximum time. If so, control transfers to step 418; otherwise, control returns to step 412. In step 414, control determines whether the derivative has returned above zero after being below zero in step 412. If so, control transfers to step 420; otherwise, control transfers to step 422.

As in step 412, control may evaluate multiple derivatives in step 414 to ensure that the derivative has reliably increased above zero. In step 422, control determines whether the timer has exceeded the predetermined maximum time. If so, control transfers to step 418; otherwise, control returns to step 414. In step 420, control reports the timer value as the notch time and control stops. In step 418, control reports the predetermined maximum time as the notch time and control stops.

Figure 7A:
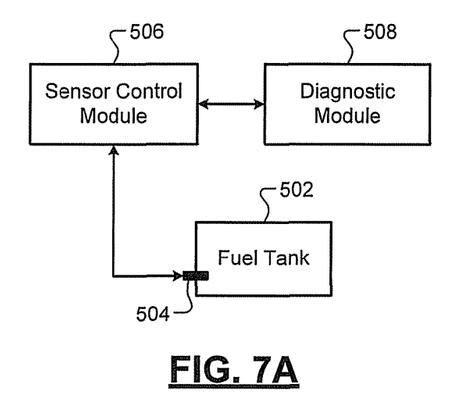
FIGS. 7A-7C are functional block diagrams of additional sensor systems according to the principles of the present disclosure.
Figure 7B:
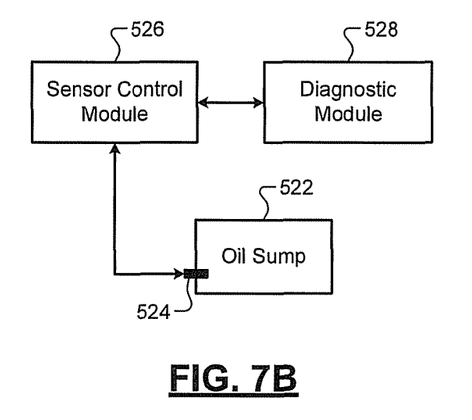
Figure 7C:
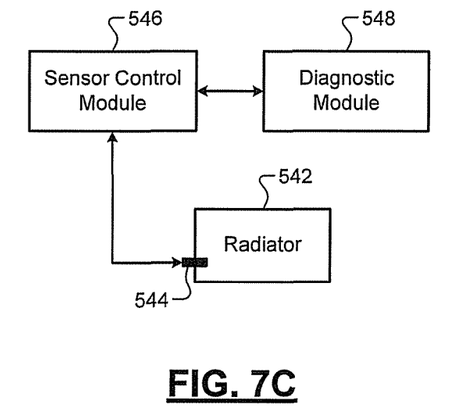

Referring now to FIGS. 7A-7C, the principles of the present disclosure can be implemented in various vehicle systems. For example only, whenever viscosity can be used to differentiate between different fluids, a sensor system as described in the present application can be implemented to measure viscosity. Viscosity may indicate which variety of a desired fluid is present. Additionally, viscosity may indicate presence of an undesired fluid or the absence of the desired fluid. Further, viscosity may indicate when properties of the desired fluid have been compromised.

For example only, FIG. 7A depicts a system for detecting water in a fuel tank 502. A sensor 504 is located in the fuel tank 502, and a sensor control module 506 analyzes readings from the sensor 504 to determine viscosity of the fluid in the fuel tank 502. If a viscosity indicative of water is measured, a diagnostic module 508 may alert an operator or a mechanic. In addition, remedial action may be performed, such as operating an engine in a reduced power mode or limiting the speed of the engine.

For example only, FIG. 7B depicts a system for detecting water or glycol in an oil supply, such as an oil sump 522. A sensor 524 is located in the oil sump 522, and a sensor control module 526 analyzes readings from the sensor 524 to determine viscosity of the fluid in the oil sump 522. If a viscosity indicative of water or glycol is measured, a diagnostic module 528 may alert an operator or a mechanic. In addition, remedial action may be performed, such as operating an engine in a reduced power mode or limiting the speed of the engine.

For example only, FIG. 7C depicts a system for detecting oil in a cooling system component, such as a radiator 542. A sensor 544 is located in the radiator 542, and a sensor control module 546 analyzes readings from the sensor 544 to determine viscosity of the fluid in the radiator 542. If a viscosity indicative of oil is measured, a diagnostic module 548 may alert an operator or a mechanic. In addition, remedial action may be performed, such as operating an engine in a reduced power mode or limiting the speed of the engine.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A sensor system comprising:
   a sensor that includes an electrically actuated moving member, wherein the sensor is in fluid communication with a reservoir of a separator that separates a first fluid from a fuel; and
   a control module that selectively causes current to be supplied to the sensor to actuate the member, that measures the current, that determines a parameter of the current, and that identifies one of presence and absence of the first fluid in the reservoir based on the parameter.

2. The sensor system of claim 1 wherein the parameter is based on a time of a local minimum of the current while the member is actuating.

3. The sensor system of claim 2 wherein the parameter is based on a time delay between a trigger time and the time of the local minimum, wherein the control module causes current to be supplied to the sensor at the trigger time.

4. The sensor system of claim 1 wherein the member is actuated to a first position when current is supplied and returns to a second position when current is not supplied.

5. The sensor system of claim 1 wherein fluid is forced through an orifice when the member is actuated.

6. The sensor system of claim 1 wherein the control module identifies presence of the first fluid when the parameter is one of less than and greater than a predetermined value.

7. The sensor system of claim 1 wherein the control module identifies the fuel as one of N varieties of fuel based on the parameter, wherein N is an integer greater than one.

8. The sensor system of claim 7 further comprising a storage module that stores parameter levels corresponding to each of the N varieties of fuel, wherein the control module identifies the fuel as one of the N varieties of fuel based on a comparison of the parameter and the parameter levels.

9. The sensor system of claim 1 wherein current is supplied to the member from a power supply and the control module compensates the parameter based on at least one of temperature and a measured voltage of the power supply.

10. The sensor system of claim 1 wherein the first fluid is one of water and air.

11. A method comprising:
    selectively causing current to be supplied to a sensor to actuate a movable member of the sensor, wherein the sensor is in fluid communication with a reservoir of a separator that separates a first fluid from a fuel;
    measuring the current supplied to the sensor;
    determining a parameter of the current; and
    identifying one of presence and absence of the first fluid in the reservoir based on the parameter.

12. The method of claim 11 wherein the parameter is based on a time of a local minimum of the current while the member is actuating.

13. The method of claim 12 wherein the parameter is based on a time delay between a trigger time and the time of the local minimum, wherein the current is caused to be supplied to the sensor at the trigger time.

14. The method of claim 11 wherein the member is actuated to a first position when current is supplied and returns to a second position when current is not supplied.

15. The method of claim 11 wherein fluid is forced through an orifice when the member is actuated.

16. The method of claim 11 further comprising identifying presence of the first fluid when the parameter is one of less than and greater than a predetermined value.

17. The method of claim 11 further comprising identifying the fuel as one of N varieties of fuel based on the parameter, wherein N is an integer greater than one.

18. The method of claim 17 further comprising:
    storing parameter levels corresponding to each of the N varieties of fuel; and
    identifying the fuel as one of the N varieties of fuel based on a comparison of the parameter and the parameter levels.

19. The method of claim 11 wherein current is supplied to the member from a power supply and further comprising compensating the parameter based on at least one of temperature and a measured voltage of the power supply.

20. The method of claim 11 wherein the first fluid is one of water and air.

* * * * *